United States Patent [19]
Medri et al.

[11] Patent Number: 5,110,584
[45] Date of Patent: May 5, 1992

[54] SCENTED NAIL ENAMELS CONTAINING ESSENTIAL OILS

[75] Inventors: Mario W. Medri; Nelly Medri, both of Millburn, N.J.

[73] Assignee: Consumer Products Corporation, N.Y.

[21] Appl. No.: 601,296

[22] Filed: Oct. 22, 1990

[51] Int. Cl.$^5$ .................. A61K 7/043; A61K 35/78; A61K 47/38; C11B 9/00
[52] U.S. Cl. ........................ 424/61; 424/401; 424/195.1
[58] Field of Search .................. 424/401, 61

[56] References Cited
FOREIGN PATENT DOCUMENTS 0138134 10/1979 Japan.
0730095 5/1955 United Kingdom.

OTHER PUBLICATIONS

Perfume & Flavor Chemicals, Steffen Arctander 1969.
Encyclopedia Brittanica, 8 pp. 715–716, 1963.

Primary Examiner—Thorman K. Page
Assistant Examiner—E. J. Webman
Attorney, Agent, or Firm—Franklyn Schoenberg

[57] ABSTRACT

A liquid fingernail cosmetic composition is provided containing at least one nail enamel film former resin, at least one organic solvent and at least one essential oil or essence component in an amount sufficient, upon activation, to provide an enhanced fragrance scent for a sustained period of time, e.g., at least about 24 hours, said essential oil or fragrance essence being activated by the formation of a nail enamel film from said coating composition.

4 Claims, No Drawings

SCENTED NAIL ENAMELS CONTAINING ESSENTIAL OILS

FIELD OF THE INVENTION

The present invention relates to cosmetic compositions and, more particularly, to nail enamel cosmetic compositions useful for application to human fingernails and toenails which provide the various requirements for the desired visual appearance together with a fragrance which enhances the cosmetic attributes of the nail enamel for an extended period of time.

BACKGROUND OF THE INVENTION

It has been common practice for humans to apply fingernail cosmetics generally referred to as nail enamel or nail polish coating compositions to the exposed surfaces of the fingernails and/or toenails for improving the appearance thereof as an adjunct to improving the general well-being and appearance of the individual.

A variety of fingernail cosmetic compositions are known and have been used over the years for beautifying or treating human fingernails and toenails. Conventional fingernail cosmetic compositions contain organic solvents and various polymeric materials including synthetic resins such as alkyd resins, polyvinyl acetate and polyester, and cellulose derivatives such as nitrocellulose and cellulose acetate as the basic or film forming component. For many years, nitrocellulose has been the most widely used film forming component although as disclosed, for example, in U.S. Pat. Nos. 3,483,289; 3,927,203; 4,126,675; 4,166,110; 4,179,304; and 4,409,203, it has been proposed to use other film forming materials in addition to or in replacement of the nitrocellulose, but none have received widespread public acceptance. However, recent improvements in the properties of solvent-type fingernail cosmetics, particularly to the nitrocellulose enamels, have led to such fingernail cosmetics becoming increasingly indispensible items among make-up cosmetics. Heretofore, the properties generally deemed necessary for fingernail cosmetics relate to the physical characteristics of the nail enamel film and the perceived visual appearance afforded thereby, i.e., stability against separation, ease of application, good coating gloss, durability and resistance to peeling. Coating compositions which serve to protect the nails against damage such as prevention of splitting and the like are also receiving increasing attention.

While fingernail cosmetic compositions typically have been directed to enhancing personal appearance by focusing on one of the senses, that of sight, it is known that an indispensible element of many make-up cosmetics and their commercial acceptance and importance in the process of imparting enhanced perceived personal appearance involves an additional dimension of sensory perception, that of smell. This is evidenced by the wide use of perfume and cologne products with particular characteristic scents, and the concern with the odor or scent perceived by the user and others, of other make-up cosmetics wherein small amounts of "fragrances" are conventionally used to mask odors perceived as being "undesirable". In this connection, objections have been raised to the "undesirable" odors emitted by the organic solvents and resin components in fingernail coating compositions and the solvent used to remove such coating compositions from the nails.

Various suggestions for overcoming or limiting "objectionable" odors in fingernail cosmetics have been disclosed, for example, in U.S. Pat. Nos. 1,878,103; 3,686,701; 3,729,569; and 4,197,212 including the use of microencapsulated and gelled formulations and/or particular combinations of solvents and film forming components; incorporating small amounts of "fragrances" in the nail enamel and/or the enamel remover compositions and the like. However, such suggestions are directed to masking the "unpleasant" odors emitted by the solvents or coating compositions during the application thereof to the fingernails or subsequent hardening of the fingernail coating, and no fingernail cosmetic compositions have been proposed in which the film coatings are intended to emit any scent other than residual "fragrances" which generally persist for only a short period of time to mask any "objectionable" residual solvent or resin odors.

It would be highly desirable if fingernail cosmetics were available which offer to the user an additional dimension by which to achieve the objective of imparting an enhanced perception of personal appearance and general well being. By virtue of adding the element of fragrance scent or the like to that already imparted visually by the fingernail cosmetic composition, the objective of enhancing the users personal appearance by make-up cosmetics is offered a significant further dimension. Particularly desirable would be fingernail cosmetics which fulfill all the necessary physical characteristics for enhancing the visual appearance of the user while emitting a sustained desired fragrance scent which withstood the usual activities including washing and could be perceived until the nail enamel coating was removed, and even more advantageous if the scents emitted were complementary to other fragrance scents used in make-up cosmetics, including perfumes and colognes.

SUMMARY OF THE INVENTION

It is, accordingly, an object of the present invention to provide a fingernail cosmetic composition which, in addition to being useful for visually enhancing the positive perception of personal appearance of human fingernails and/or toenails, will emit a desired fragrance scent which could be perceived by the user and others for an extended period, and preferably could be perceived until the coating film was removed by the user.

It is a further object of the present invention to provide a fingernail cosmetic composition which includes the necessary ingredients for fulfilling the physical characteristics of the nail enamel film to enhance the desired visual appearance of human fingernails and/or toenails and, in addition, emits a desired fragrance scent which could be perceived by the user and other for an extended period of time, and at least the time desired by the user as evidenced by maintaining the coating composition on the nails.

It is a still further object of the present invention to provide a nail enamel coating composition which is durable, dries quickly, can be readily and uniformly applied, has a good gloss, adheres well, is easily removed by solvents and forms a film coating which emits a sustained fragrance scent for an extended period of time and will not be effected by water or soap.

It is another object of the present invention to provide a nail enamel coating composition which can be formulated to provide a clear film or can be modified to provide a colored transparent or a colored opaque film or pearlescent film as desired and upon formation of a film on the surface of human fingernails and/or toenails will emit a desired enhanced fragrance scent which can be perceived for an extended period of time. e.g., at least 24 hours, which fragrance scent is complementary to the scents emitted by perfume and cologne products and/or make-up cosmetics.

Still another object of the present invention is to provide a nail enamel coating composition which can be formulated to provide a substantially clear film which emits a desired enhanced fragrance scent for a sustained period and can be applied to the surface of a human fingernail or other substrate.

In accordance with the present invention, there is provided a liquid fingernail cosmetic composition comprising at least one nail enamel film former resin, at least one organic solvent and at least one essential oil or essence component in an amount sufficient, upon activation, to provide an enhanced fragrance scent for a sustained period of time, e.g., at least about 24 hours, said essential oil or fragrance essence being activated by the formation of a nail enamel film from said coating composition.

Other objects, features and advantages of the present invention will be readily apparent from the following detailed description.

DESCRIPTION OF THE PREFERRED EMBODIMENTS

The present invention is predicated upon the discovery that providing fingernail cosmetic compositions for beautifying the visual appearance of human fingernails and/or toenails which include an essential oil or essence component will surprisingly impart an additional dimension to such make-up cosmetics in the process of enhancing perceived personal appearance. The composition of the invention, when applied, not only thoroughly fulfills all the characteristics for making-up the nails to impart an enhanced visual appearance but also emits a characteristic scent which can be perceived by the user for an extended period of time and, if desired, can be coordinated with characteristic fragrances and scents of other make-up cosmetics including perfumes and colognes. The fragrance or scent will, in general, not be perceived until application of the coating composition to the surface of the nail and the hardening thereof in a conventional manner by evaporation of the organic solvents or the like. The film once formed on the nails emits an enhanced scent which will be sustained generally for at least 24 hours even after washing or performing usual kitchen work and, preferably, until the coating film is removed by the user.

The fingernail cosmetic composition of the present invention comprises a fingernail cosmetic composition containing at least one resin and at least one organic solvent suitable for application to human fingernails and toenails for protection and/or beautification thereof having incorporated therein an essential oil or essence in an amount sufficient to emit an enhanced fragrance scent for a sustained period of time, e.g., at least 24 hours, from a nail enamel film formed by the application of said fingernail cosmetic composition to the surface of nails or any substrate.

Conventional fingernail cosmetic compositions contain resins and organic solvents as main components and any such conventional solvent-type fingernail cosmetic composition may be suitable for use in the compositions of the present invention. These compositions are, for example, those based on nitrocellulose. The nitrocellulose, if incorporated in the compositions of the present invention, may be any known nitrocellulose conventionally used in such compositions. Such nitrocellulose can be used alone or in combination. The amount of nitrocellulose incorporated typically ranges from about 5 to 25% by weight relative to the total weight of the composition.

The resins used in the composition of the present invention may be any known resins conventionally used in fingernail cosmetic compositions such as, for example, alkyd resin, acrylic resin, polyester resin, sucrose resin, sulfonamide resin, rosin resin or the like. Such resins can be used alone or in combination. The amount of resin used ranges in general from about 10% to 40% by weight, or if nitrocellulose is employed, from about 3% to 15% by weight, relative to the total weight of the composition.

The organic solvent used in the present composition may be any known organic solvent conventionally used in such a composition, e.g., esters, alcohols, hydrocarbons, or the like. For example, there may be used ethyl acetate, butyl acetate, amyl acetate, ethyl alcohol, isopropyl alcohol, butyl alcohol, acetone, toluene and mixtures thereof. The amount of the organic solvent used ranges from about 30% to 85% by weight, relative to the total weight of the composition.

There may also be optionally incorporated into compositions of the present invention for fulfilling the physical characteristics of the nail enamel film, conventional modifiers such as a plasticizer, e.g., dibutyl phthalate, dioctyl phthalate, tributyl citrate, acetyl tributyl citrate, acetyl triethyl citrate, or camphor; a pigment; dyestuff; pearling agent; gelling agent based on organo-modified bentonite; ultraviolet light absorber or the like. It is necessary to ensure that the use of such optional ingredients do not interfere with the achievements of the objects of the present invention.

There are a great variety of natural and synthetic scents of fragrances and flavors generally known in the form of blends or as individually identifiable aromatics recognizable by their characteristic scents or as trade name perfumes or colognes. Scents are typically available as natural and synthetic essential oils or essences, and any known essential oil or essence or blends thereof may be suitable for use in compositions of the present invention. As indicated, the fingernail compositions of the invention, surprisingly, can be formulated to form a nail enamel coating film which emits a particular enhanced characteristic scent and the particular essential oil, essence or blend thereof used may be selected to effect such a desired effect. Thus, in certain preferred embodiments for enhancing the overall appearance of a user, fingernail cosmetic compositions of the invention may be prepared wherein particular essential oils or essences are used and the nail enamel film emits scents which may be complementary to or coordinated with the fragrance or scent of other make-up cosmetics including perfumes and colognes.

The color of essential oils and essences can also vary and, in general, such color variation will not adversely affect the desired color of nail enamel films formed from fingernail cosmetic compositions of the invention. However, the color of some essential oils or essences may interfere with the clarity of clear fingernail cosmetic compositions or the films formed therefrom. Thus, color may also be a factor in the selection of essential oils or essences as well as the scent. While, as indicated, any available essential oil or essence may be suitable for use, when a particular characteristic scent and/or color is desired for achieving a particular effect, the selection thereof can be readily determined by one skilled in the art using conventional technology. The amount of essential oil or essence used in preparing compositions of the invention can vary depending on the particular essential oil or essence used, the fragrance scent desired, and the resin and solvent composition of the base fingernail cosmetic composition. In general, it is very important that at least 3% to about 20%, and preferably from about 5% to about 10%, by weight of essential oil or essence relative to the total weight of the composition should be used in the fingernail cosmetic composition of the invention in order that a sustained fragrance scent of desired intensity will be emitted by the nail enamel film for at least 24 hours, and preferably longer as herein indicated.

The fingernail cosmetic composition of the present invention may be prepared by adding to the conventional fingernail cosmetic composition the essential oil, essence or blend thereof and agitating to effect a homogeneous mixture, or the essential oil, essence or blend thereof may be added during any convenient step in the process of preparation of the conventional fingernail cosmetic composition.

The invention will now be further illustrated by the description of certain specific examples of its practice which are not intended to be limiting.

EXAMPLE 1

Fingernail cosmetic compositions are prepared from the following formulations:

| Sample | Ingredients | % by weight |
|---|---|---|
| A | Conventional Fingernail Composition | 95.0 |
|   | Fragrance Oil Blend A | 5.0 |
|   |   | 100.0 |
| B | Conventional Fingernail Composition | 94.0 |
|   | Fragrance Oil Blend B | 6.0 |
|   |   | 100.0 |
| C | Conventional Fingernail Composition | 91.0 |
|   | Fragrance Oil Blend C | 9.0 |
|   |   | 100.0 |
| D | Conventional Fingernail Composition | 92.0 |
|   | Fragrance Oil Blend D | 8.0 |
|   |   | 100.0 |

The Conventional Fingernail Composition used in all the above samples is a clear nail enamel composition available from Donna Lee Inc., Newark, N.J.; Fragrance A is Belmay 9463 (Belmay Co., Long Island City, N.Y.; Fragrance B is De Laire 26258 (De Laire, New York, N.Y.); Fragrance C is #434910 (Felton Worldwide, Brooklyn, N.Y.; Fragrance D is Artificial Grape Flavor 82504 (International Flavor & Fragrance, Dayton, N.J.).

All samples of the example form a clear film when applied to fingernails which emit an enhanced scent for at least 24 hours after application of the coating composition.

EXAMPLE 2

Fingernail cosmetic compositions are prepared from the following formulations:

| Sample | Ingredients | % by weight |
|---|---|---|
| A | Conventional Fingernail Composition | 95.0 |
|   | Fragrance Oil Blend A | 5.0 |
|   |   | 100.0 |
| B | Conventional Fingernail Composition | 93.0 |
|   | Fragrance Oil Blend B | 7.0 |
|   |   | 100.0 |
| C | Conventional Fingernail Composition | 90.0 |
|   | Fragrance Oil Blend C | 10.0 |
|   |   | 100.0 |
| D | Conventional Fingernail Composition | 91.0 |
|   | Fragrance Oil Blend D | 9.0 |
|   |   | 100.0 |

The Conventional Fingernail Composition used in all the above samples is a "Romantic Mauve Creme" nail enamel composition available from Maybelline, Memphis, Tenn.; Fragrance A is #3071-AL (International Flavor & Fragrance, Dayton, N.J.); Fragrance B is #434910 (Felton Worldwide, Brooklyn, N.Y.); Fragrance C is De Laire 26190 (De Laire, New York, N.Y.); Fragrance D is Artificial Cherry Flavor 28781 (Felton Worldwide, Brooklyn, N.Y.).

All samples of the example form a colored film when applied to fingernails which emit an enhanced scent for at least 24 hours after application of the coating composition.

EXAMPLE 3

Fingernail cosmetic compositions are prepared from the following formulations:

| Ingredients | % by weight |
|---|---|
| 1 Conventional Fingernail Composition | 96.0 |
| Fragrance Oil Blend | 4.0 |
|   | 100.0 |
| 2 Conventional Fingernail Composition | 94.0 |
| Fragrance Oil Blend | 6.0 |
|   | 100.0 |
| 3 Conventional Fingernail Composition | 92.0 |
| Fragrance Oil Blend | 8.0 |
|   | 100.0 |
| 4 Conventional Fingernail Composition | 90.0 |
| Fragrance Oil Blend | 10.0 |
|   | 100.0 |

All fingernail compositions of this example use the Conventional Fingernail Composition of Example 1. A series of fingernail compositions using the above formulations are prepared with each of the following Fragrance Oil Blends as follows:

Samples A 1-4 Fragrance Oil #9463 (Belmay Co.)
Samples B 1-4 Fragrance Oil #9475 (Belmay Co.)
Samples C 1-4 Fragrance Oil #9489 (Belmay Co.)

The various samples are evaluated for scent release time duration and the results are summarized below.

| | Sample | | | | | | | |
|---|---|---|---|---|---|---|---|---|
| | A-1 | | A-2 | | A-3 | | A-4 | |
| | | | | Coats (No.) | | | | |
| Time (hrs) | 1 | 2 | 1 | 2 | 1 | 2 | 1 | 2 |
| 0 | 3 | 4 | 4 | 5 | 6 | 7 | 7 | 7 |
| 12 | 2 | 3 | 3 | 4 | 5 | 6 | 6 | 6 |
| 24 | 1 | 2 | 2 | 3 | 3 | 5 | 5 | 6 |
| 36 | 0 | 0 | 0 | 2 | 3 | 4 | 4 | 5 |
| 48 |   |   |   | 2 | 2 | 4 | 3 | 4 |

Sample

-continued

| | B-1 | | B-2 | | B-3 | | B-4 | |
|---|---|---|---|---|---|---|---|---|
| | Coats (No.) | | | | | | | |
| Time (hrs) | 1 | 2 | 1 | 2 | 1 | 2 | 1 | 2 |
| 0 | 3 | 4 | 4 | 5 | 6 | 7 | 7 | 7 |
| 12 | 2 | 3 | 3 | 4 | 5 | 6 | 6 | 6 |
| 24 | 0 | 2 | 2 | 4 | 4 | 5 | 5 | 6 |
| 36 | 0 | 1 | 1 | 3 | 2 | 4 | 4 | 5 |
| 48 | | 0 | 0 | 2 | 2 | 4 | 3 | 4 |

| | Sample | | | | | | | |
|---|---|---|---|---|---|---|---|---|
| | C-1 | | C-2 | | C-3 | | C-4 | |
| | Coats (No.) | | | | | | | |
| Time (hrs) | 1 | 2 | 1 | 2 | 1 | 2 | 1 | 2 |
| 0 | 5 | 6 | 6 | 7 | 7 | 8 | 8 | 8 |
| 12 | 4 | 5 | 5 | 6 | 6 | 7 | 7 | 7 |
| 24 | 3 | 4 | 4 | 6 | 5 | 6 | 6 | 6 |
| 36 | 2 | 3 | 3 | 5 | 4 | 5 | 5 | 6 |
| 48 | 0 | 2 | 2 | 4 | 3 | 5 | 4 | 5 |

All samples of this Example exhibit similar qualities of coating film clarity and enhanced scent emission after storage of the samples in closed containers for an extended period of time.

Although the fingernail cosmetic compositions of the invention have been illustrated in the foregoing detailed description in the context of certain specific fingernail coating compositions and fragrance scents, it should be appreciated that other variations may be made. Accordingly, the invention is not intended to be limited to the specific embodiments or examples set forth in the specification, but rather is limited only by the appended claims.

What is claimed is:

1. A fingernail cosmetic composition comprising a fingernail cosmetic composition suitable for application to human fingernail and toenails for protection and beautification thereof containing from about 5% to about 40% by weight of at least one resin and from about 30% to about 85% by weight of at least one organic solvent having incorporated therein an essential oil or blends thereof in an amount of at least 6% to about 20% by weight relative to the total weight of the composition sufficient to emit an enhanced fragrance scent for at least 24 hours after a nail enamel film is formed by application of said fingernail cosmetic composition to the surface of nails or any substrate.

2. The fingernail cosmetic composition as claimed in claim 1, wherein a nail enamel film formed by application of said fingernail cosmetic composition to the surface of nails emits an enhanced fragrance scent of a make-up cosmetic or flavor type after a nail enamel film is formed until said film is removed by user.

3. The fingernail cosmetic composition as claimed in claim 1, wherein said resin is nitrocellulose.

4. The fingernail cosmetic composition as claimed in claim 1, wherein said organic solvent includes a solvent selected from the group consisting ethyl acetate, butyl acetate, amyl acetate, acetone, toluene and mixtures thereof.

* * * * *